US011556806B2

(12) United States Patent
Vrouwenvelder et al.

(10) Patent No.: US 11,556,806 B2
(45) Date of Patent: Jan. 17, 2023

(54) USING MACHINE LEARNING TO FACILITATE DESIGN AND IMPLEMENTATION OF A CLINICAL TRIAL WITH A HIGH LIKELIHOOD OF SUCCESS

(71) Applicant: International Business Machines Corporation, Armonk, NY (US)

(72) Inventors: Adrian Vrouwenvelder, Chapel Hill, NC (US); Stephen Alan Carraway, Durham, NC (US); John Hefferman, Durham, NC (US); Kimberly Diane Kenna, Cary, NC (US)

(73) Assignee: MERATIVE US L.P., Ann Arbor, MI (US)

(*) Notice: Subject to any disclaimer, the term of this patent is extended or adjusted under 35 U.S.C. 154(b) by 337 days.

(21) Appl. No.: 15/931,739

(22) Filed: May 14, 2020

(65) Prior Publication Data
US 2021/0357769 A1 Nov. 18, 2021

(51) Int. Cl.
*G06F 17/00* (2019.01)
*G06N 5/02* (2006.01)
(Continued)

(52) U.S. Cl.
CPC ........... *G06N 5/025* (2013.01); *G06K 9/6215* (2013.01); *G06K 9/6256* (2013.01); *G06N 20/00* (2019.01); *G16H 10/20* (2018.01)

(58) Field of Classification Search
CPC ........ G06N 5/025; G06N 20/00; G16H 10/20; G06K 9/6215; G06K 9/6256
(Continued)

(56) References Cited

U.S. PATENT DOCUMENTS 7,415,447 B2 8/2008 Shiffman et al.
8,032,545 B2 10/2011 Setimi
(Continued)

FOREIGN PATENT DOCUMENTS

WO 2015102844 A1 7/2015
WO 2019182297 A1 9/2019
WO 2020033754 A1 2/2020

OTHER PUBLICATIONS

List of IBM Patents or Patent Applications Treated as Related, filed Jun. 2, 2020.
(Continued)

*Primary Examiner* — Isaac M Woo
(74) *Attorney, Agent, or Firm* — Edell, Shapiro & Finnan, LLC

(57) ABSTRACT

A method, computing platform, and computer program product are provided. A computing platform receives, for a clinical trial, study design information including a set of parameters related to a success of a clinical trial and factors related to a relevance of the parameters. The computing platform provides multiple sets of varying parameter values. At least one trained machine learning model is applied to the study design information including the sets of parameter values to predict multiple success scores including a predicted overall success score. The computing platform outputs the provided set of values for the set of parameters that are associated with the at least one trained machine learning model predicting a best overall success score for the clinical trial.

20 Claims, 10 Drawing Sheets

(51) Int. Cl.
  *G06N 20/00* (2019.01)
  *G16H 10/20* (2018.01)
  *G06K 9/62* (2022.01)

(58) Field of Classification Search
  USPC .................................... 707/600–899; 706/47
  See application file for complete search history.

(56) References Cited

U.S. PATENT DOCUMENTS

| | | | |
|---|---|---|---|
| 8,386,416 | B2 | 2/2013 | Levin, II et al. |
| 8,793,145 | B2 | 7/2014 | Kahn et al. |
| 9,600,637 | B2 | 3/2017 | Harder et al. |
| 10,255,273 | B2 | 4/2019 | Chakraborty et al. |
| 10,366,781 | B1 | 7/2019 | Menon et al. |
| 11,328,796 | B1 | 5/2022 | Jain et al. |
| 2005/0256380 | A1 | 11/2005 | Nourie et al. |
| 2006/0036471 | A1 | 2/2006 | Sanjay-Gopal et al. |
| 2006/0129326 | A1 | 6/2006 | Braconnier et al. |
| 2006/0282244 | A1 | 12/2006 | Chotai et al. |
| 2007/0294111 | A1 | 12/2007 | Settimi |
| 2009/0112618 | A1 | 4/2009 | Johnson et al. |
| 2010/0114594 | A1 | 5/2010 | Schultz |
| 2010/0250273 | A1 | 9/2010 | Li |
| 2014/0214441 | A1 | 7/2014 | Young et al. |
| 2014/0278469 | A1 | 9/2014 | Secci |
| 2014/0324553 | A1 | 10/2014 | Rosenberg |
| 2014/0344208 | A1* | 11/2014 | Ghasemzadeh ........ G16H 50/50 706/52 |
| 2014/0358571 | A1 | 12/2014 | Geleijnse et al. |
| 2015/0220868 | A1 | 8/2015 | Elashoff |
| 2016/0042155 | A1 | 2/2016 | Li |
| 2016/0203296 | A1 | 7/2016 | Bound et al. |
| 2018/0039763 | A1 | 2/2018 | Tidor |
| 2018/0181573 | A1 | 6/2018 | Zhao |
| 2018/0301209 | A1 | 10/2018 | Kim et al. |
| 2018/0310890 | A1 | 11/2018 | Li |
| 2019/0080785 | A1 | 3/2019 | Li |
| 2019/0131001 | A1 | 5/2019 | Fox et al. |
| 2019/0206521 | A1 | 7/2019 | Walpole et al. |
| 2019/0306093 | A1 | 10/2019 | Schilling et al. |
| 2019/0311787 | A1 | 10/2019 | Graiver et al. |
| 2020/0042923 | A1 | 2/2020 | Zhou et al. |
| 2020/0211680 | A1 | 7/2020 | Sablinski et al. |
| 2021/0357778 | A1 | 11/2021 | Vrouwenvelder et al. |
| 2021/0358576 | A1 | 11/2021 | Vrouwenvelder et al. |

OTHER PUBLICATIONS

Getz et al., "Assessing Patient Participation Burden Based on Protocol Design Characteristics", Therapeutic Innovation & Regulatory Science 2020, vol. 54(3) 598-604. (Year: 2020).

Borno et al., "At What Cost to Clinical Trial Enrollment? A Retrospective Study of Patient Travel Burden in Cancer Clinical Trials", The Oncologist 2018;23:1242-1249 (Year: 2018).

Medidate Solutionsm :"Using Patient Burden Evaluation to Improve Clinical Trial Planning and Execution", May 2018 White Paper, pp. 1-7. (Year: 2018).

Harrer et al., "Artificial Intelligence for Clinical Trial Design," Trends in Pharmacological Sciences, Aug. 2019, vol. 10, No. 8 (Year: 2019), 15 pages.

"Study Shows that with Clinical Trial Participation Comes the Burden of Travel," ClinEdge Staff, http://clin-edge.com/news/study-shows-that-with-clinical-trial-participation-comes-the-burden-of-travel (Year: 2018), 3 pages.

B. Pflugeisen, et al., "Assessment of clinical trial participant patient satisfaction: a call to action", Trials 17, 483 (2016). https://doi.org/10.1186/s13063-016-1616-6, 7 pages.

* cited by examiner

USING MACHINE LEARNING TO FACILITATE DESIGN AND IMPLEMENTATION OF A CLINICAL TRIAL WITH A HIGH LIKELIHOOD OF SUCCESS

BACKGROUND

1. Technical Field

Present invention embodiments relate to evaluating varying sets of parameter values for a given set of clinical trial parameters and providing real-time feedback regarding a set of the varying sets of parameter values for a clinical trial with a high likelihood of success. In particular, the present invention embodiments relate to using at least one trained machine learning model to evaluate varying sets of parameter values for a given set of clinical trial parameters to facilitate design and implementation of a clinical trial with a high likelihood of success.

2. Discussion of the Related Art

Clinical study designers have difficulty designing visit schedules and visit content for a clinical trial such that a sufficient amount of data is collected without overburdening participants. Collecting too many data points as well as collecting the data points too frequently may place too much of a burden on participants such that participant recruitment and retention may be adversely affected. Collecting too few data points or collecting the data points too infrequently may adversely affect success of the clinical trial.

To determine an optimal visit schedule and optimal visit content for a clinical trial involving a targeted patient population, a clinical study designer should consider a number of different factors such as, for example, health of the participants, a nature of treatments during a clinical trial, a nature of a disease or a condition being treated, invasiveness of procedures on the participants, expected travel time for the participants, and a best method for monitoring participant compliance (e.g., more/less frequent visits or automated monitoring).

SUMMARY

According to one embodiment of the present invention, a computer-implemented method is provided for monitoring clinical trial protocols. A computing platform receives study design information for a clinical trial. The study design information includes a set of parameters related to a success of the clinical trial and factors related to a relevance of the parameters. The computing platform provides multiple sets of values for the set of parameters, wherein the multiple sets vary the values for the set of parameters. At least one trained machine learning model is applied to the study design information, which includes the provided sets of values, to predict multiple success scores including a predicted overall success score. The computing platform outputs the provided set of values for the set of parameters that are associated with the at least one trained machine learning model predicting a best overall success score for the clinical trial.

According to a second embodiment of the present invention, a computing platform for monitoring clinical trial protocols is provided. The computing platform includes at least one processor and at least one memory connected with the at least one processor. The at least one processor is configured to perform a number of steps. According to the steps, study design information for a clinical trial is received. The study design information includes a set of parameters related to a success of the clinical trial and factors related to a relevance of the parameters. Multiple sets of values are provided for the set of parameters, wherein the multiple sets vary the values for the sets of parameters. At least one trained machine learning model is applied to the study design information, which includes the provided sets of values, to predict a score for each of multiple success scores including a predicted overall success score. The provided set of values for the set of parameters that are associated with the at least one trained machine learning model predicting a best overall success score for the clinical trial are output as values of the set of parameters for the clinical trial.

According to a third embodiment of the present invention, a computer program product for assessing clinical trial protocols is provided. The computer program product includes one or more computer readable storage media having program instructions collectively stored on the one or more computer readable storage media. The program instructions are executable by at least one process of a computing platform to cause the computing platform to perform a number of steps. According to the steps, study design information for a clinical trial is received. The study design information includes a set of parameters related to a success of the clinical trial and factors related to a relevance of the parameters. Multiple sets of values are provided for the set of parameters. At least one trained machine learning model is applied to the study design information, which includes the provided sets of values, to predict multiple success scores including a predicted overall success score. The provided set of values for the set of parameters that are associated with the at least one trained machine learning model predicting a best overall success score for the clinical trial are output as values of the set of parameters for the clinical trial.

BRIEF DESCRIPTION OF THE DRAWINGS

Generally, like reference numerals in the various figures are utilized to designate like components.

DETAILED DESCRIPTION

Figure 1:
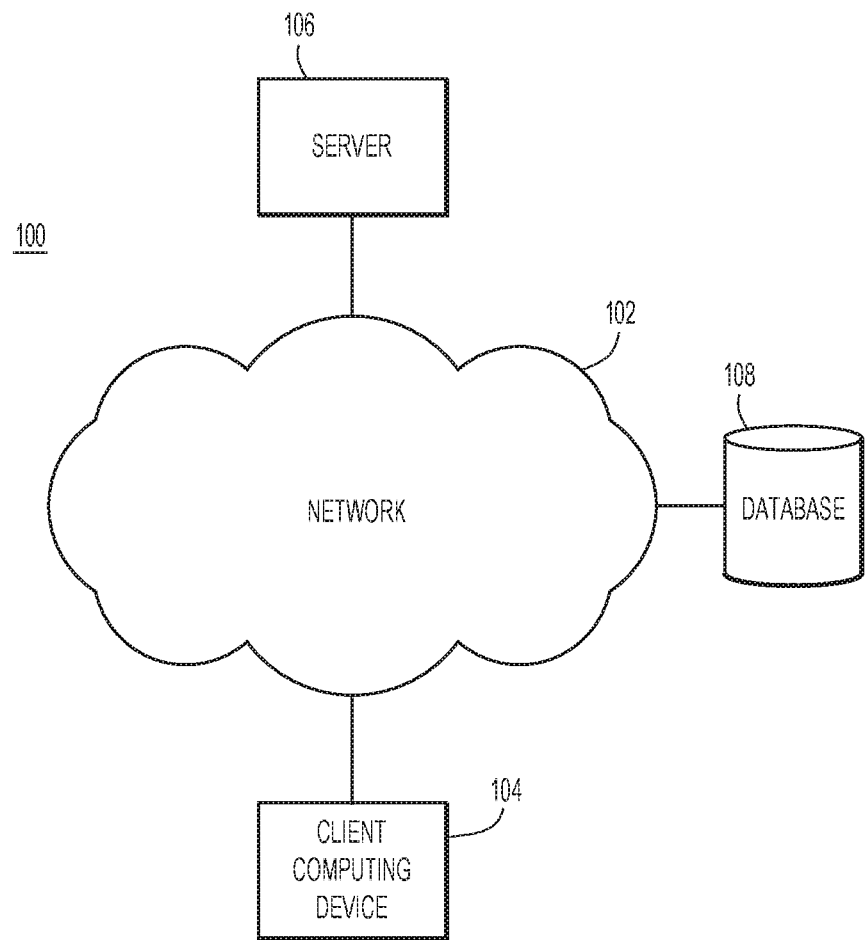
FIG. 1 is a diagrammatic illustration of an example computing environment according to an embodiment of the present invention.

In various embodiments of the present invention, a machine learning model is trained to predict an overall clinical trial success score and related success scores based on a set of parameters and corresponding values as well as derivative factors. In some embodiments, the related success scores may include, but not be limited to, a participant recruitment rate, a participant retention rate and a data quality score.

Embodiments may include a number of different input parameters. For example, some of the input parameters may include meta-factors and other input parameters that may help determine a likelihood of success of a clinical trial.

Meta-factors may determine a relevance of some parameters. Example meta-factors may include, but not be limited to, a particular therapeutic area, a specific condition, a severity of progression of a disease or a condition, and demographics. The demographics may include, but not be limited to, participant age, participant gender, family income, etc.

The input parameters that may help determine a success of a clinical trial may include, but not be limited to, a total number of visits per participant, a duration of the clinical trial, an average duration of each visit, an average frequency of visits per period of time (e.g., per month, per year, etc.), an average duration of each task, a score reflecting how a given procedure made participants feel, and overall number of data points collected, participant characteristics (e.g., normalizations of age, mobility, mental acuity, etc.), trial specific risk factors (e.g., hypertension, etc.), and number of queries raised during the clinical trial (e.g., an excessive number of queries, as compared with similar clinical trials, may indicate that the clinical trial questions are difficult to understand, which may correlate with adversely affected data quality).

During a study, participants may be asked to complete a survey. In some embodiments, a number of factors related to the survey also may help determine whether a clinical trial will be successful. The factors may include, but not be limited to, an amount of time for a participant to enter a response (e.g., too short of a time may indicate that a question was too easy or that the participant really didn't consider the question, too long of a time may indicate that the question was too difficult), a frequency of participant reported outcomes (e.g., frequency may be too burdensome or may not provide enough data points), type of outcomes reported (e.g., condition improving, condition deteriorating, etc.), and examination of text of a response when available.

For a clinical trial, a score may be calculated representing per-visit task density, which may be comprised of a combination of a number of tasks per participant visit and a level of intensity for each task indicating whether a task is easy for a participant or difficult and painful for the participant. Participants are more likely to tolerate a low-level intensity task rather than a high-level intensity task. Therefore, in a clinical trial, a clinical study designer may schedule, for example, ten low-level intensity tasks in a single visit, but only one high-level intensity task. An outcome of each task may be taken into consideration when predicting a likelihood of success for the clinical trial.

The per-visit task density may be constructed from a quantization of invasiveness of a procedure being performed (considering needles, drugs, exercise, immobilization, disruption of natural schedule, etc.) across an overall number of tasks. In various embodiments, the per-visit task density may be normalized. For example, based on ranges of scores for the per-visit task density, the per-visit task density may be normalized in some embodiments as extremely easy, easy, average, slightly difficult, difficult, extremely difficult, etc.

A travel score that combines travel cost (e.g., tolls, fare cards, fuel), distance, expected traffic conditions, and travel time may be calculated and provided as input into a machine learning model. A participant may live only a few minutes away, but may have to pay a high toll such as, for example, for a tunnel or a bridge, or the participant may be within walking distance, in which case travel time may be 15 minutes of pleasant walking, which is quite different from 15 minutes of stressful rush-hour traffic. The above-mentioned factors may be combined into a simple weighted formula to compute a score for helping to predict an overall clinical trial outcome.

An example environment 100 for use with present invention embodiments is illustrated in FIG. 1. Specifically, the environment includes a computing platform, which may include one or more servers 106. Environment 100 further may include one or more client or end-user computing devices 104, and a database management system 108, which may be included as part of one or more servers 106 or may be executing on a separate system connected to network 102. Server 106, client computing device 104, and database management system 108 may be remote from each other and may communicate over a network 102. Network 102 may be implemented by any number of any suitable communications media (e.g., wide area network (WAN), local area network (LAN), Internet, Intranet, etc.). Alternatively, server 106, client computing device 104, and database management system 108 may be local to each other and may communicate via any appropriate local communication medium (e.g., local area network (LAN), hardwire, wireless link, Intranet, etc.).

Client computing device 104 enable a user such as, for example, a clinical study designer, to submit input parameters and corresponding parameter values for a clinical trial. The input parameters and corresponding values may be provided to client computing device 104 by the user via a user interface, which may be a graphical user interface, a textual user interface, a speech recognition user interface, or other user interface. The input parameters and the corresponding values may be provided by client computing device 104 to server 106 via network 102. Server 106 may receive the input parameters and the corresponding values and may apply the input parameters and the corresponding values to at least one machine learning model trained to predict an overall success score and other clinical trial success scores including, but not limited to, a data quality score, a participant retention score, and a participant recruitment score. The predicted overall success score may be based on a combination of the data quality score, the participant retention score, and the participant recruitment score. Server 106 may provide client computing device 104 output from the at least one machine learning model for presentation to the user via client computing device 104. The output may include, for example, the above-mentioned scores presented in a graphical format. Other embodiments may present the output in other forms such as, for example, displayed text and speech, as well as other forms.

Database management system 108 may store various information for analysis by the at least one machine learning model such as, for example, the input parameters and their corresponding values as well as other information. Database management system 108 may be implemented by any conventional or other database or storage unit, may be local to or remote from server 106 and client computing device 104, and may communicate via any appropriate communication medium (e.g., local area network (LAN), wide area network (WAN), Internet, hardwire, wireless link, Intranet, etc.).

The client computing device 104 may present a graphical user interface (e.g., GUI, etc.) or other user interface (e.g., command line prompts, menu screens, etc.) to solicit information from the user pertaining to the clinical trial input parameters and the corresponding values, and may provide results from applying the input parameters and the corresponding values to the at least one machine learning model.

Figure 2:
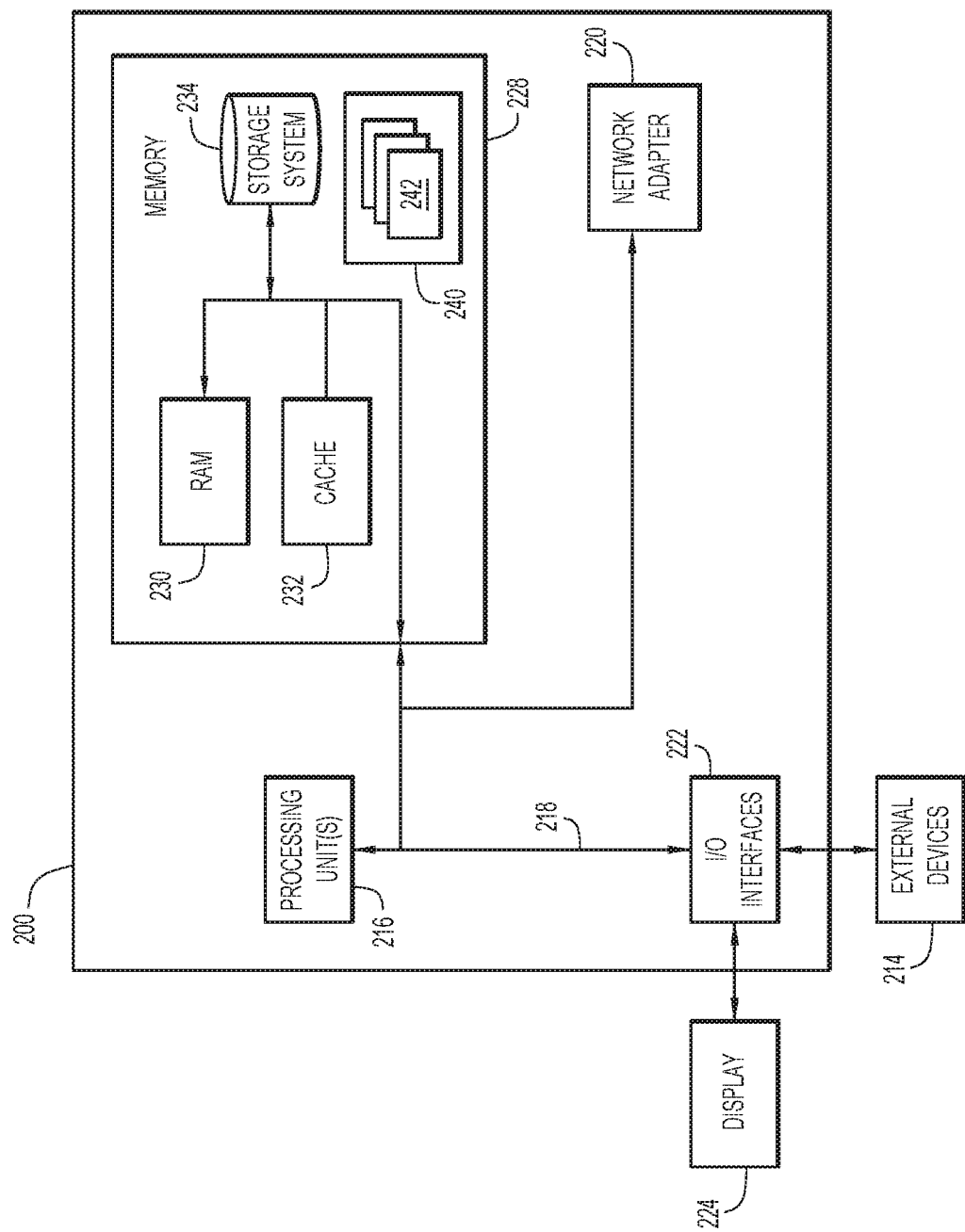
FIG. 2 is a block diagram of an example computing device according to an embodiment of the present invention.

Referring now to FIG. 2, a schematic of an example computer system 200 is shown, which may implement any of server 106 and client computer device 104 in various embodiments. Computer system 200 is shown in a form of a general-purpose computing device. Components of computer system 200 may include, but are not limited to, one or more processors or processing units 216, a system memory 228, and a bus 218 that couples various system components including system memory 228 to one or more processing units 216.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 200 may include a variety of computer system readable media. Such media may be any available media that is accessible by computer system 200, and may include both volatile and non-volatile media, removable and non-removable media.

System memory 228 can include computer system readable media in the form of volatile memory, such as random access memory (RAM) 230 and/or cache memory 232. Computer system 200 may further include other removable/non-removable, volatile/non-volatile computer system storage media. By way of example only, storage system 234 can be provided for reading from and writing to a non-removable, non-volatile magnetic medium (not shown, which may include a "hard drive" or a Secure Digital (SD) card). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 228 may include at least one program product having a set (e.g., at least one) of program modules that are configured to carry out the functions of embodiments of the invention.

Program/utility 240, having a set (at least one) of program modules 242, may be stored in memory 228 by way of example, and not limitation, as well as an operating system, one or more application programs, other program modules, and program data. Each of the operating system, the one or more application programs, the other program modules, and the program data or some combination thereof, may include an implementation of a networking environment. Program modules 242 generally carry out the functions and/or methodologies of embodiments of the invention as described herein.

Computer system 200 may also communicate with one or more external devices 214 such as a keyboard, a pointing device, one or more displays 224, one or more devices that enable a user to interact with computer system 200, and/or any devices (e.g., network card, modem, etc.) that enable computer system 200 to communicate with one or more other computing devices. Such communication can occur via Input/Output (I/O) interfaces 222. Still yet, computer system 200 can communicate with one or more networks such as a local area network (LAN), a general wide area network (WAN), and/or a public network (e.g., the Internet) via network adapter 220. As depicted, network adapter 220 communicates with the other components of computer system 200 via bus 218. It should be understood that, although not shown, other hardware and/or software components could be used in conjunction with computer system 200. Examples, include, but are not limited to: a microphone, one or more speakers, microcode, device drivers, redundant processing units, external disk drive arrays, RAID systems, tape drives, and data archival storage systems, etc.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 3:
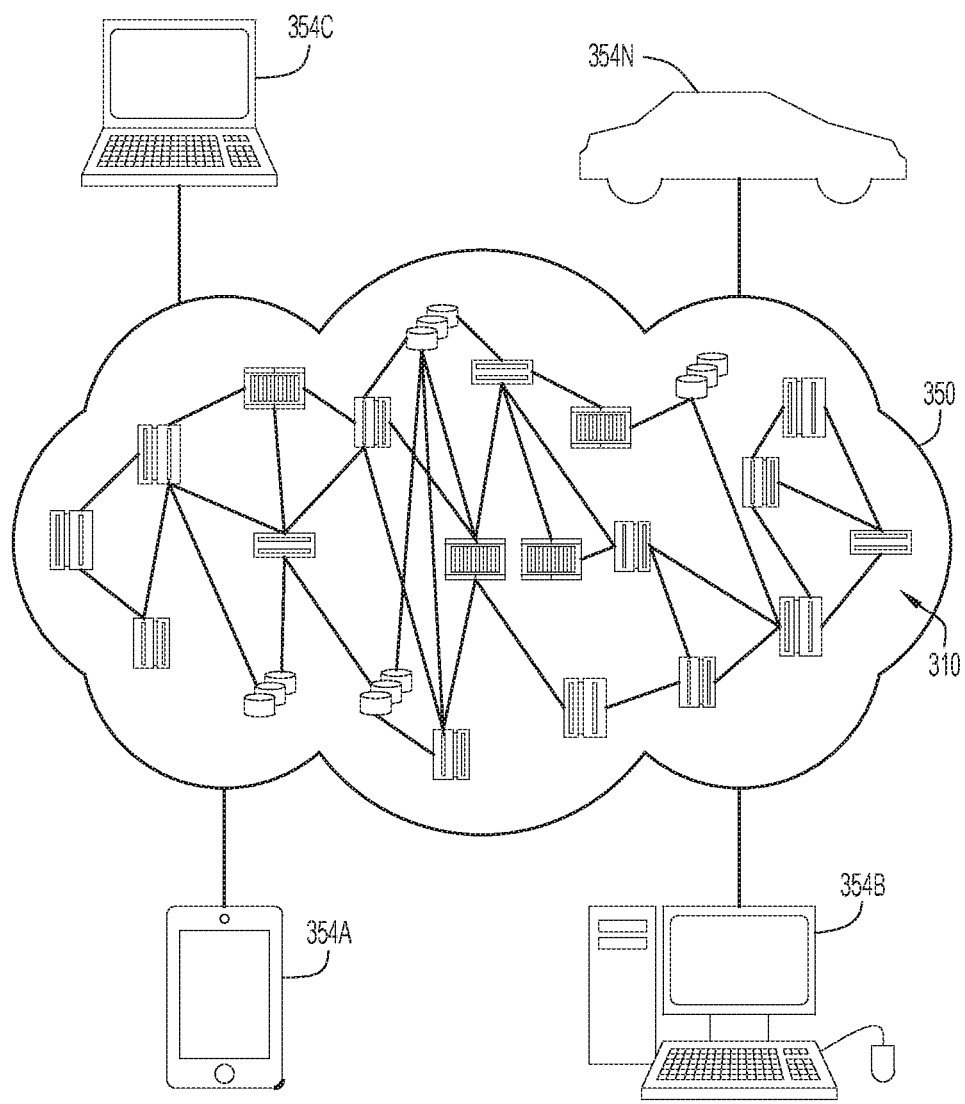
FIG. 3 illustrates an example cloud computing environment according to some embodiments of the invention.

Referring now to FIG. 3, an illustrative cloud computing environment 350 is depicted. As shown, cloud computing environment 350 includes one or more cloud computing nodes 310 with which local computing devices used by cloud consumers, such as, for example, personal digital assistant (PDA) or cellular telephone 354A, desktop computer 354B, laptop computer 354C, and/or automobile computer system 354N may communicate. Nodes 310 may communicate with one another. They may be grouped (not shown) physically or virtually, in one or more networks, such as Private, Community, Public, or Hybrid clouds as described hereinabove, or a combination thereof. This allows cloud computing environment 350 to offer infrastructure, platforms and/or software as services for which a cloud consumer does not need to maintain resources on a local computing device. It is understood that the types of computing devices 354A-N shown in FIG. 3 are intended to be illustrative only and that computing nodes 310 and cloud computing environment 350 can communicate with any type of computerized device over any type of network and/or network addressable connection (e.g., using a web browser).

Figure 4:
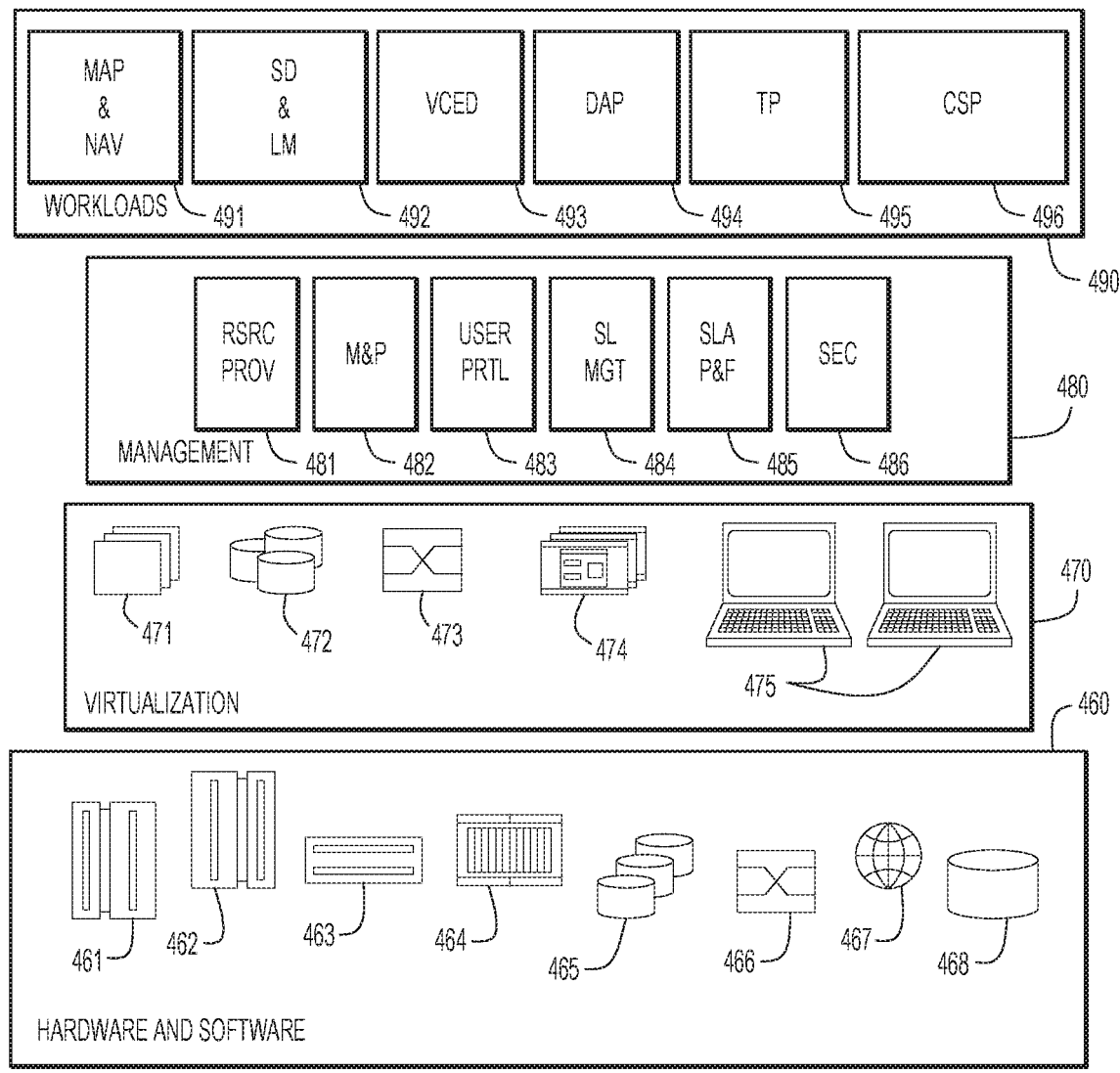
FIG. 4 illustrates an example set of functional abstraction layers that may be provided by the example cloud computing environment of FIG. 3 according to some embodiments.

Referring now to FIG. 4, a set of functional abstraction layers provided by cloud computing environment 350 (FIG. 3) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 460 includes hardware and software components. Examples of hardware components include: mainframes 461; RISC (Reduced Instruction Set computer) architecture based servers 462; servers 463; blade servers 464; storage devices 465; and networks and networking components 466. In some embodiments, software components include network application server software 467 and database software 468.

Virtualization layer 470 provides an abstraction layer from which the following examples of virtual entities may be provided: virtual servers 471; virtual storage 472; virtual networks 473, including virtual private networks; virtual applications and operating systems 474; and virtual clients 475.

In one example, management layer 480 may provide the functions described below. Resource provisioning 481 provides dynamic procurement of computing resources and other resources that are utilized to perform tasks within the cloud computing environment. Metering and pricing 482 provide cost tracking as resources are utilized within the cloud computing environment, and billing or invoicing for consumption of these resources. In one example, these resources may include application software licenses. User portal 483 provides access to the cloud computing environment for consumers and system administrators. Service level management 484 provides cloud computing resource allocation and management such that required service levels are met. Service Level Agreement (SLA) planning and fulfillment 485 provide pre-arrangement for, and procurement of, cloud computing resources for which a future requirement is anticipated in accordance with an SLA. Security (SEC) 486 provides identity verification for cloud consumers and tasks, as well as protection for data and other resources.

Workloads layer 490 provides examples of functionality for which the cloud computing environment may be utilized. Examples of workloads and functions which may be provided from this layer include: mapping and navigation 491; software development and lifecycle management 492; virtual classroom education delivery 493; data analytics processing 494; transaction processing 495; and clinical study processing (CSP) 496 for receiving input parameters and corresponding values for a clinical trial and for predicting a likelihood of success of the clinical trial.

Figure 5:
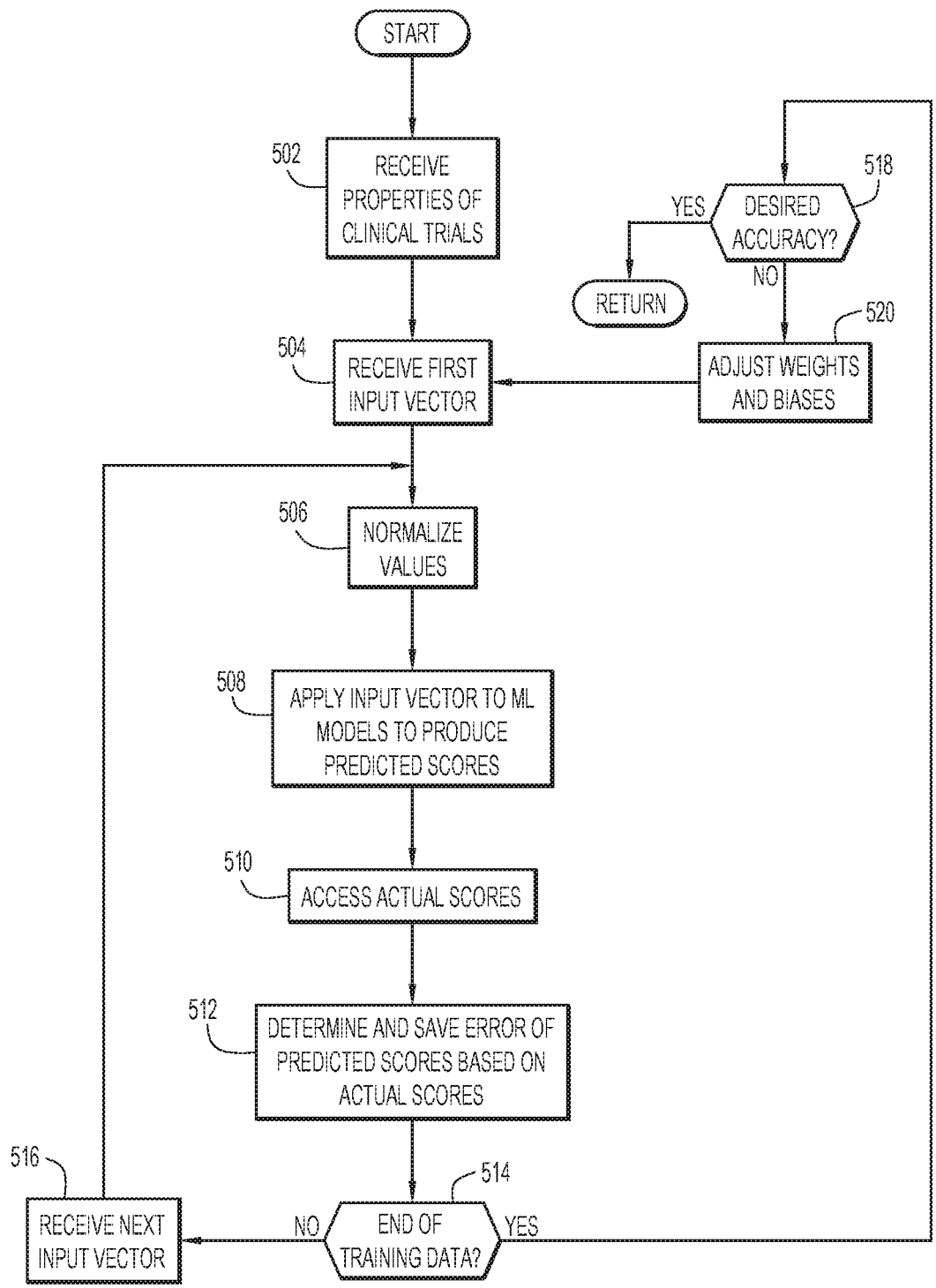
FIG. 5 is a flowchart of an example process for training one or more machine learning models according to embodiments of the present invention.

FIG. 5 is a flowchart of an example process for training one or more machine learning models to predict scores such as, for example, a data quality score, a retention score, a recruitment score, and a predicted success score for a clinical trial. This process is known as supervised machine learning. Training data includes properties of actual clinical trials and actual scores related to the clinical trials.

In some embodiments, multiple machine learning models may be used. For example, a first machine learning model may calculate a predicted data quality score based on values of the input parameters. A second machine learning model may calculate a predicted participant retention score based on the values of the input parameters. A third machine learning model may calculate participant recruitment scores based on the values of the input parameters. A fourth machine learning model may calculate a likelihood of success of a clinical trial based on a combination of the data quality score, the participant retention score, and the participant recruitment score.

The process may begin by receiving properties of the clinical trials included in the training data (act 502). The properties may include input parameters that may be similar to input parameters of clinical trials that will be applied to the trained machine learning models. In some embodiments, the machine learning models may include a regression algorithm such as, for example, a linear regression algorithm. Further, the machine learning models of some embodiments may include a convolutional neural network (CNN). In other embodiments, another algorithm may be included in the machine learning model. Each of the machine learning models may include weights and a bias to be applied to the values of at least some of the input parameters to calculate a predicted score. The respective weights and the respective bias included in each of the machine learning models may be set to predefined values initially such as, for example, 0 or another value.

The machine learning model may be trained based on actual clinical trials with known results. To train a machine learning model, training data may include data from a number of actual clinical trials such as, for example, 10,000 clinical trials or another number of clinical trials.

After receiving the properties of the clinical trials, a first input vector of corresponding values of the input parameters may be received (act 504). The values of the input parameters then may be normalized (act 506). Alternatively, instead of normalizing values of the input parameters during the training process, the values of each input vector may be normalized before the training process.

Next, the received input vector may be applied to each of the machine learning models to produce, respectively, a data quality score, a participant retention score, a participant recruitment score, and a predicted overall success score (act 508). In at least some embodiments, the scores may be normalized in a range from 0 to 100, where 0 may be a worst score and 100 may be a best score. In other embodiments, the scores may be normalized differently.

After producing the predicted scores, actual scores for the clinical trial may be accessed (act 510) and an error may be determined and saved based on a difference between the actual scores and the predicted scores (act 512). A check may then be made to determine whether an end of the training data is reached (act 514) and, if not, a next input vector for a next clinical trial in the training data may be received (act 516). Acts 506-514 then may be performed again.

If, during act 514, the end of the training data is determined to have been reached, then a determination may be made regarding whether the predicted scores are within a desired range of accuracy (act 518). If the predicted scores are determined not to be within the desired range of accuracy, then the weights and the biases for the machine learning models may be adjusted to improve accuracy (act 520). Acts 504-520 again may be performed.

Figure 6:
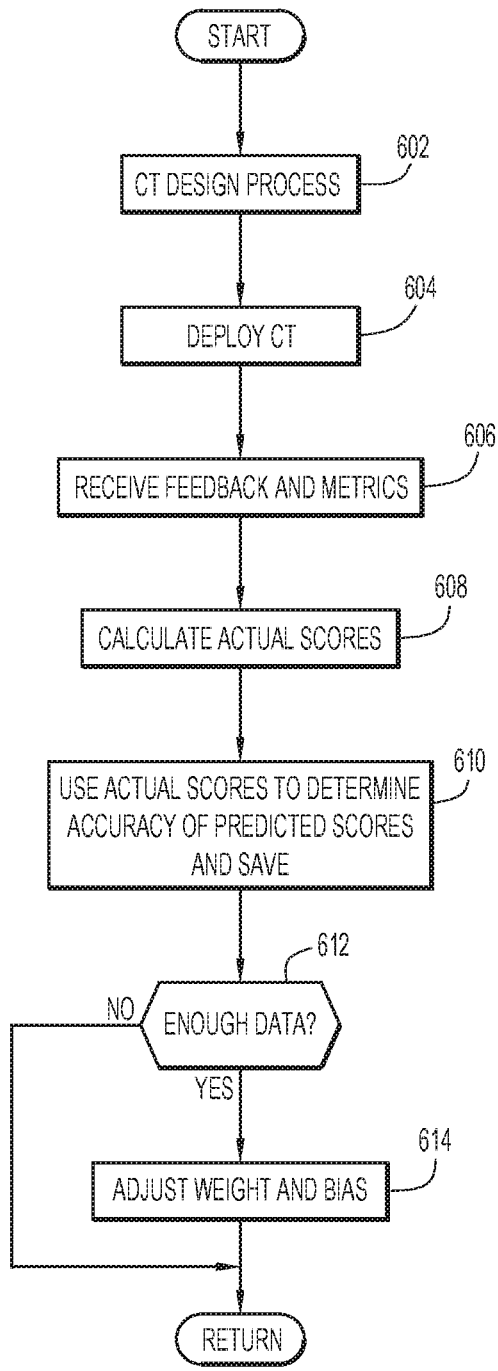
FIG. 6 is a flowchart illustrating an example process that includes designing and deploying a clinical trial and adjusting weights and a bias for at least one machine learning model.

FIG. 6 is a flowchart illustrating an example process by which trained machine learning models may be used to predict scores related to a clinical trial based on input parameters, corresponding values, and feedback and metrics associated with the clinical trial. The process may begin with a clinical trial design process in which a clinical study designer may provide clinical trial input parameters and corresponding values via a user interface of client computing device 104 (act 602). During act 602, the input parameters and corresponding values may be provided to server 106 via network 102 and server 106 may execute the trained machine learning models to predict scores for the clinical trial such as, for example, a predicted data quality score, a predicted participant retention score, a predicted participant recruitment score, and a predicted overall success score.

The clinical trial then may be deployed (act 604) and monitored. While the clinical trial is deployed, participants of the clinical trial may be asked to complete one or more surveys. While completing the one or more surveys, client computing device 104 or server 106 may measure an amount of time that a participant takes to answer respective survey questions. Further, a frequency of reported participant outcomes and type of outcomes may also be tracked and saved. When participants provide responses to survey questions, the responses may be analyzed and classified as, for example, positive, negative, or neutral. Any or all of the above-mentioned information may be included in feedback and metrics, which server 106 may provide to the machine learning models to produce an updated set of predicted scores for the clinical trial (act 606). Once the clinical trial is completed actual scores for data quality, participant retention, participant recruitment, and overall success score may be calculated (act 608) and may be used along with the predicted scores to determine accuracy of the predicted scores, which may be saved (act 610).

Next, a determination may be made regarding whether enough data has been processed and saved such that the weights and the biases of the machine learning models may be updated based on the determined accuracy of the predicted scores (act 612). In various embodiments, enough data may be determined to have been collected when predicted scores for a given number of clinical trials have been saved. In various embodiments, the given number may be 10,000, 5000, 1,000, or another number. If, during act 612, not enough data has been determined to be collected, then the process may be completed. Otherwise, the determined accuracy of predicted scores from the given number of clinical trials may be used to adjust weights and biases of the machine learning models (act 614) and the process then may be completed.

Figure 7:
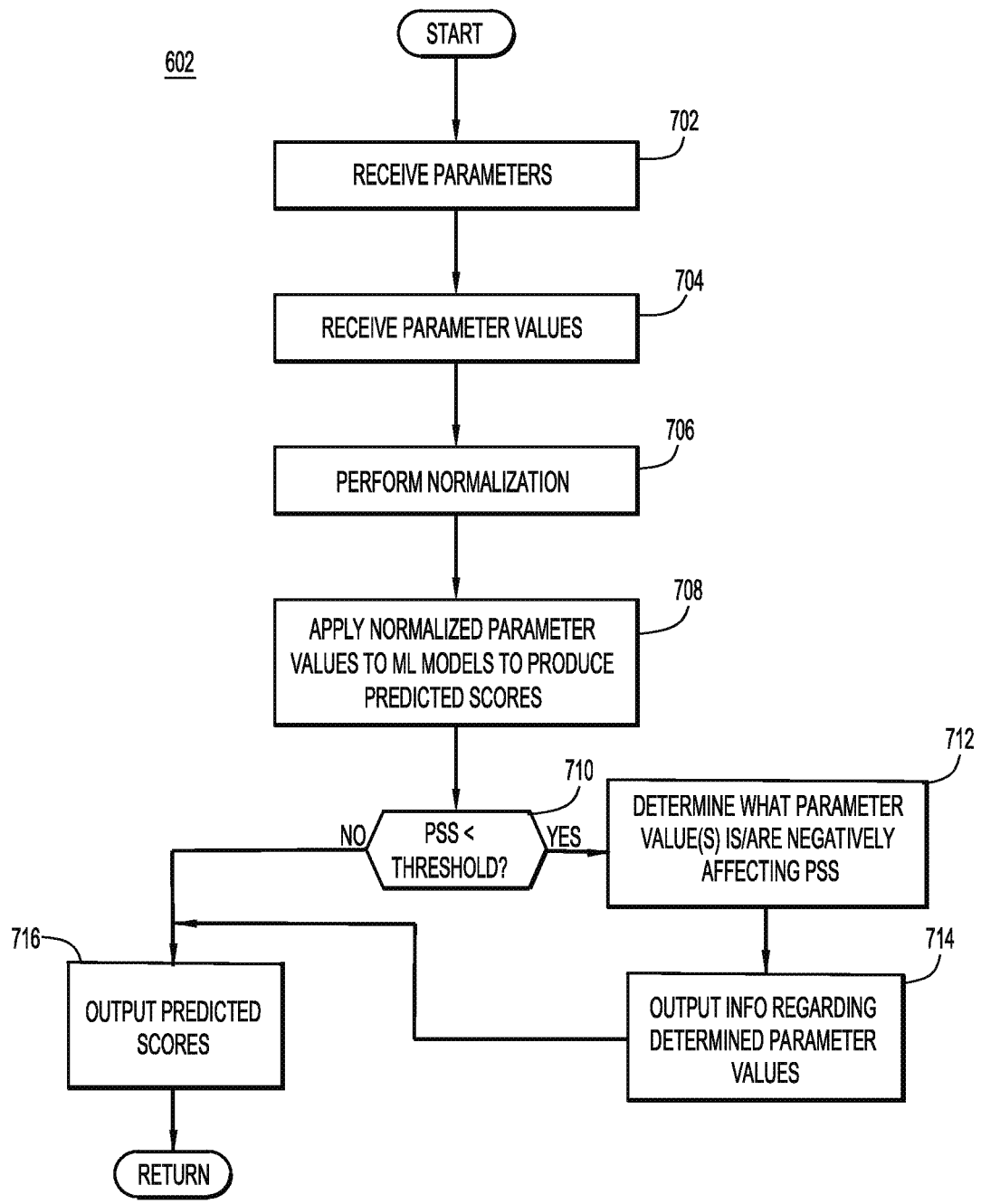
FIG. 7 illustrates a flowchart of an example process for predicting success scores during clinical trial design according to embodiments of the present invention.

FIG. 7 is a flowchart of an example process for performing act 602 to predict scores for a clinical trial. The process may begin by receiving input parameters (act 702) and corresponding values (act 704) for the clinical trial. The input parameters and the corresponding values may be provided to server 106 from client computing device 104 via network 102. A clinical study designer may provide the input parameters and the corresponding values to client computing device 104 via a user interface. Server 106 may normalize at least some of the values of the input parameters (act 706). The normalized parameter values may be applied to the trained machine learning models to produce the predicted scores, which may include but not be limited to, a predicted data quality score, a predicted participant retention score, a predicted participant recruitment score, and an overall predicted success score (act 708).

In some embodiments, if the process determines that the overall predicted success score is less than a threshold value such as, for example, 90%, 80%, or another suitable value (act 710), the process may determine, based on using one or more of the trained machine learning models, which one or more parameter values are negatively affecting the overall predicted success score (act 712). For example, the process may analyze predicted scores that are used to determine the overall predicted success score and may determine that the predicted participant retention score is lower than other predicted scores that are used to predict the overall success score. The process then may analyze the values that are applied to a model for predicting the participant retention score, and based on this model, may determine that average visit duration is negatively affecting the participant retention score. If the input parameters for the clinical trial include expected visit durations for each clinical visit of the clinical trial, the process may rank the visits by expected duration to pinpoint one or more specific visits that are lowering the participant retention rate influenced by the expected visit durations. The process then may output information regarding the parameter values having a negative effect on the overall predicted success score (act 714). For example, with respect to the above example, the process may output information indicating that a visit duration of a third and a fifth clinical visit are negatively affecting the overall predicted success score.

If, during act 710, the process determines that the overall predicted success score is not less than the threshold value, or after the process performs act 714, the process may output the predicted scores (act 716).

Figure 8:
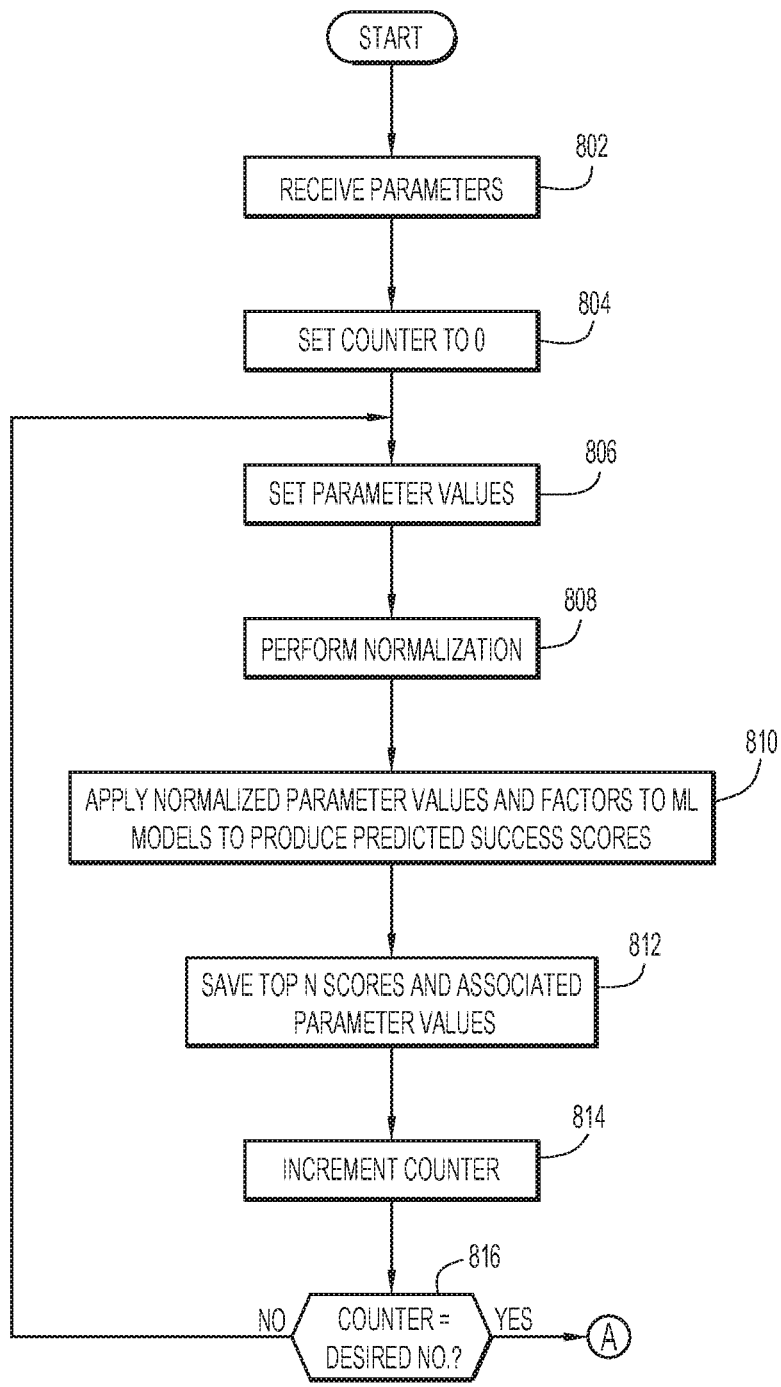
FIGS. 8-9 are flowcharts of an example process for determining parameter values for a clinical study according to an embodiment of the present invention.
Figure 9:
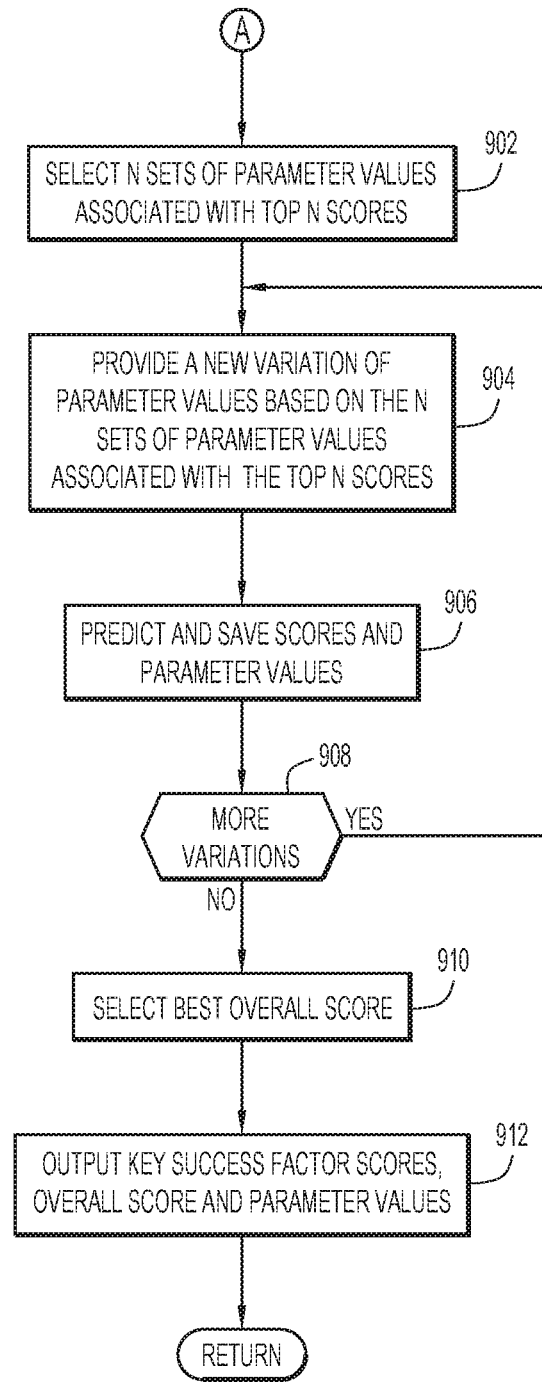

In addition to having a user provide parameter values to trained machine learning models to calculate predicted scores, some embodiments may generate varying parameter values for a given number of clinical trials to determine sets of parameter values associated with clinical trials having overall predicted success scores included in a top N of best overall predicted success scores, where N is an integer with a value greater than or equal to two. In some embodiments, N is equal to two. A set of parameter values may be determined based on the sets of parameter values with overall predicted scores included among the top N best overall predicted success scores. FIGS. 8 and 9 are flowcharts that illustrate such an example process.

The process may begin with server 108 receiving parameters from client computing device 104 via network 102 (act 802; FIG. 8). The parameters may have originally been provided by a user of client computing device 104 via a user interface.

Next, a counter may be set to zero (act 804) and server 106 may set values of the received parameters (806). In some embodiments, the values may be randomly set for each of the parameters according to a valid range of the each parameter. Normalizing of the parameter values then may be performed (act 808). For example, if average duration of each visit is a parameter, values of this parameter may be normalized to: less than 30 minutes; greater than 30 minutes and less than 60 minutes; greater than 60 minutes and less than two hours; greater than two hours and less than six hours; etc. The parameter values, including the normalized parameter values, may be applied to trained machine learning models to predict an overall success score as well as other success scores, which may include, but not be limited to, a data quality score, a participant retention score, and a participant recruitment score (act 810). If the predicted overall success score is among a top N overall success scores, then the overall predicted success score may be saved along with the other predicted scores and the parameter values (act 812). If a number of saved predicted overall success scores would become greater than N, as a result of saving a predicted overall success score, then a lowest score among the saved N predicted overall success scores may be deleted prior to saving a another predicted overall success score. The counter then may be incremented (act 814) and a determination may be made regarding whether the counter is equal to a desired number (act 816). If the counter is determined not to be equal to the desired number, then the desired number of parameter value variations had not yet been generated and processing returns to act 806 to set a variation of the parameter values (act 806) and the process may continue as previously described.

If, during act 816, the counter is determined to be equal to the desired number, then the N sets of parameter values associated with the top N predicted overall success scores may be selected (act 902; FIG. 9). A new variation of the parameter values may be generated based on the N sets of parameter values associated with the top N predicted overall scores (act 904). For example, parameter values may be selected from any of the N sets of the parameter values. The new variation of parameter values then may be applied to the trained machine learning models to predict and save the overall success score and the other scores (act 906). A determination may be made regarding whether any additional variations of the parameter values, based on the parameter values associated with the top N predicted overall success scores, are to be generated (act 908). In some embodiments, only a predefined number of variations of the parameter values are to be generated from the top N sets of parameter values. In other embodiments, all possible combinations of parameter values from the top N sets of parameter values may be generated. If more variations of the top N sets of parameter values are to be generated, then acts 904-906 again may be performed. Otherwise, a set of parameter values associated with one of the top N sets of parameter values having a best predicted overall success score may be selected (act 910) and server 106 may provide the predicted best overall success score, the other success scores and corresponding parameter values to client computing device 104 for presentation to the user (act 912).

Figure 10:
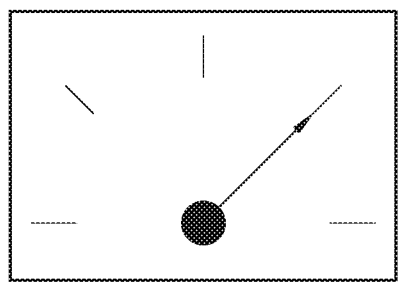
FIGS. 10-13 illustrate respective example displays of a predicted data quality score, a predicted participant retention score, a predicted participant recruitment score, and a predicted overall success score according to an embodiment of the present invention.
Figure 11:
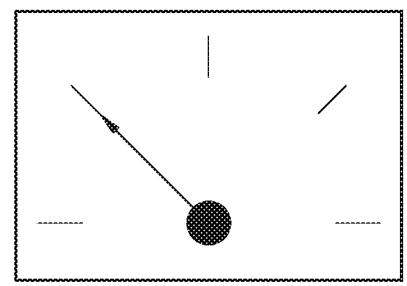
Figure 12:
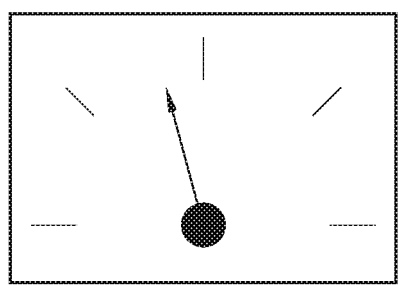
Figure 13:
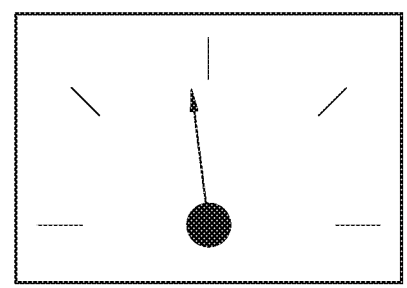

According to some embodiments, server 106 may provide predicted scores to client computing device 104 such that the predicted scores may be presented to a user of client computing device 104 via a graphical user interface. The scores may be presented in a form that resembles a fuel gauge in an automobile. For example, FIG. 10 shows a predicted data quality score as being about 75% or 0.75. FIG. 11 shows a predicted participant retention score at about 25% or 0.25. FIG. 12 shows a predicted participant recruitment score as being about 42% or 0.42. FIG. 13 shows a predicted overall success score as being about 49% or 0.49

Embodiments of the present invention describe multiple scoring factors which help to determine optimal clinical trial parameter values. Embodiments use one or more trained machine learning models to calculate scores for the multiple scoring factors such as, for example, a participant recruitment rate score, a participant retention rate score, a data quality score, and an overall success score based on the scores for the multiple scoring factors. Various embodiments of the present invention generate multiple sets of varying parameter values for a given set of clinical trial parameters and apply the varying sets of the parameter values to the one or more trained machine learning models to provide, in real-time, feedback including a set of the varying sets of parameter values having a best likelihood of success. A clinical trial is implemented using the parameter values having the best chance of success. The clinical trial may be conducted virtually (e.g., on a computer system and/or network) and/or physically for any desired item (e.g., medication, device, etc.). It will be appreciated that the embodiments described above and illustrated in the drawings represent only a few of the many ways of evaluating varying sets of parameter values for a given set of clinical trial parameters and providing real-time feedback regarding a set of the varying sets of parameter values for a clinical trial with a high likelihood of success.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, profile generation module, profile comparison module, etc.). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information (e.g., parameters and parameter values, etc.). The database system may be included within or coupled to the server and/or client systems. The database systems and/or storage structures may be remote from or local to the computer or other processing systems, and may store any desired data.

The present invention embodiments may employ any number of any type of user interface (e.g., Graphical User Interface (GUI), command-line, prompt, etc.) for obtaining or providing information, where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The present invention embodiments are not limited to the specific tasks or algorithms described above, but may be utilized for evaluating varying sets of parameter values for a given set of parameters for a number of different projects and for providing real-time feedback including a set of the varying set of parameter values for implementing a project with a high likelihood of success.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for monitoring clinical trial protocols, the computer-implemented method comprising:
   receiving, by a computing platform, study design information for a clinical trial, the study design information including a set of parameters related to a success of the clinical trial and factors related to a relevance of the parameters;
   providing, by the computing platform, plural sets of values for the set of parameters, wherein the plural sets of values are produced by varying values for the set of parameters, and wherein the values for the set of parameters are used to implement the clinical trial;
   applying, by the computing platform, at least one trained machine learning model to the study design information including the provided sets of values to predict a score for each of a plurality of success scores including a predicted overall success score;
   determining, by the computing platform, the provided set of values for the set of parameters that are associated with the at least one trained machine learning model predicting a best overall success score for the clinical trial; and
   outputting, by the computing platform, the determined set of values for implementing the clinical trial.

2. The computer-implemented method of claim 1, further comprising:
   selecting a second plurality of sets of the provided values associated with next greatest predicted overall success scores; and
   providing new variations of a set of values for the set of parameters based on the selected second plurality of sets of the provided values, and
   applying the new variations of the set of values for the set of parameters to predict a score for the each of the plurality of success scores, wherein
   the outputting, by the computing platform, further comprises outputting the set of values of the new variations associated with a best predicted overall success score.

3. The computer-implemented method of claim 1, further comprising:
   providing a user interface to allow a user to modify the study design information.

4. The computer-implemented method of claim 3, further comprising:
   responsive to the user modifying the study design information, applying, by the computing platform, the at least one trained machine learning model to the modified study design information to predict the score for the each of the plurality of success scores.

5. The computer-implemented method of claim 4, further comprising:
   determining weights and a bias adjustment applied by the at least one trained machine learning model to the set of parameters for predicting the score for the each of the plurality of success scores.

6. The computer-implemented method of claim 1, wherein the factors related to the relevance of the parameters include a therapeutic area, a specific condition, a severity of progression of the condition, and demographics.

7. The computer-implemented method of claim 1, wherein:
   the set of parameters related to the success of the clinical trial include a total number of clinical trial visits, a duration of the clinical trial, an average duration of the clinical trial visits, an average frequency of the clinical trial visits over a given period of time, an average duration of each task, a number of data points collected during the clinical trial, and clinical trial risk factors, and
   the plurality of success scores include a data quality score, a participant retention score, and a participant recruitment score.

8. A computing platform for monitoring clinical trial protocols, the computing platform comprising:
   at least one processor; and
   at least one memory connected with the at least one processor, wherein the at least one processor is configured to perform:
   receiving study design information for a clinical trial, the study design information including a set of parameters related to a success of the clinical trial and factors related to a relevance of the parameters;
   providing plural sets of values for the set of parameters, wherein the plural sets of values are produced by varying values for the set of parameters, and wherein the values for the set of parameters are used to implement the clinical trial;
   applying at least one trained machine learning model to the study design information including the provided sets of values to predict a score for each of a plurality of success scores including a predicted overall success score;
   determining the provided set of values for the set of parameters that are associated with the at least one trained machine learning model predicting a best overall success score for the clinical trial; and
   outputting the determined set of values for implementing the clinical trial.

9. The computing platform of claim 8, wherein the at least one processor is further configured to perform:
   selecting a second plurality of sets of the provided values associated with next greatest predicted overall success scores;
   providing new variations of a set of values for the set of parameters based on the selected second plurality of sets of the provided values, and
   applying the new variations of the set of values for the set of parameters to predict a score for the each of the plurality of success factors, wherein
   the outputting further comprises outputting the set of values of the new variations associated with a best predicted overall success score.

10. The computing platform of claim 8, wherein the at least one processor is further configured to perform:
   providing a user interface to allow a user to modify the study design information;
   responsive to the user modifying the study design information, applying the at least one trained machine learning model to the modified study design information to predict the score for the each of the plurality of success scores; and outputting the predicted score for the each of the plurality of success scores responsive to applying the at least one trained machine learning model to the modified design information.

11. The computing platform of claim 10, wherein the at least one processor is further configured to perform:

determining weights and a bias adjustment applied by the at least one trained machine learning model to a set of parameters of the modified design information for predicting the score for the each of the plurality of success scores.

12. The computing platform of claim 8, wherein the factors related to the relevance of the parameters include a therapeutic area, a specific condition, a severity of progression of the condition, and demographics.

13. The computing platform of claim 8, wherein:

the set of parameters related to the success of the clinical trial include a total number of clinical trial visits, a duration of the clinical trial, an average duration of the clinical trial visits, an average frequency of the clinical trial visits over a given period of time, an average duration of each task, a number of data points collected during the clinical trial, and clinical trial risk factors.

14. The computing platform of claim 8, wherein the at least one processor is further configured to perform:

calculating a per-visit task density score based on an average number of tasks per visit and a level intensity of each of the tasks, wherein a predicted participant retention rate score is based, at least partly, on the per-visit task density score, wherein the plurality of success scores includes the participant retention rate score.

15. The computing platform of claim 8, wherein the at least one processor is further configured to perform:

calculating an average travel score for participants of the clinical trial based on travel cost, a distance to travel, travel time, and expected traffic level; and determining the predicted overall success score based, at least partly, on the average travel score.

16. A computer program product for assessing clinical trial protocols, the computer program product comprising one or more computer readable storage media having program instructions collectively stored on the one or more computer readable storage media, the program instructions executable by at least one processor of a computing platform to cause the computing platform to:

receive study design information for a clinical trial, the study design information including a set of parameters related to a success of the clinical trial and factors related to a relevance of the parameters;

provide plural sets of values for the set of parameters, wherein the plural sets of values are produced by varying values for the set of parameters, and wherein the values for the set of parameters are used to implement the clinical trial;

apply at least one trained machine learning model to the study design information including the provided sets of values to predict a score for each of a plurality of success scores including a predicted overall success score;

determine the provided set of values for the set of parameters that are associated with the at least one trained machine learning model predicting a best overall success score for the clinical trial; and output the determined set of values for implementing the clinical trial.

17. The computer program product of claim 16, wherein the program instructions are further executable by the at least one processor of the computing platform to:

provide output to cause a display device to visually display graphical gauges indicating a corresponding score for a participant retention rate, a participant recruitment rate, a data quality score, and the predicted overall success score.

18. The computer program product of claim 16, wherein the program instructions are further executable by the at least one processor of the computing platform to:

receive modified study design information from a client computing device, the modified study design information having been modified via a user interface of the client computing device;

responsive to the receiving of the modified study design information, apply the at least one trained machine learning model to the modified study design information to predict the score for the each of the plurality of success scores including the predicted overall success score;

responsive to determining that the predicted overall success score is less than a threshold value:

determine which one or more parameter values are negatively affecting the predicted overall success score, and output information regarding the determined one or more parameter values; and output the predicted score for the each of the plurality of success scores responsive to applying the at least one trained machine learning model to the modified study design information.

19. The computer program product of claim 16, wherein the program instructions are further executable by the at least one processor of the computing platform to:

calculate a survey-related score based, at least partly, on measured participant response times, a frequency of participant reported outcomes, outcomes reported, and analysis of textual responses when available;

determine the predicted overall success score based, at least partly, on the survey-related score and the each score for the plurality of success scores; and output the predicted overall success score and the each score for the plurality of success scores.

20. The computer program product of claim 16, wherein the program instructions are further executable by the at least one processor of the computing platform to:

determine a number of queries received during the clinical trial, wherein a predicted score for a data quality score is based, at least partly, on the number of queries received, wherein the plurality of success scores includes the data quality score.

* * * * *